United States Patent [19]

Torres et al.

[11] Patent Number: 5,046,614
[45] Date of Patent: Sep. 10, 1991

[54] NEEDLE DISPOSAL CONTAINER

[76] Inventors: Jonathan K. Torres, 172 Harland Rd., Norwich, Conn. 06360; John M. Wiprud, 1662 S. 116th #3, West Allis, Wis. 53214

[21] Appl. No.: 559,398

[22] Filed: Jul. 26, 1990

Related U.S. Application Data

[63] Continuation of Ser. No. 359,708, May 31, 1989, abandoned.

[51] Int. Cl.⁵ ............................................. B65D 25/00
[52] U.S. Cl. .................................. 206/366; 220/252; 220/908
[58] Field of Search ............... 206/366, 63.5; 270/908, 270/910; 220/252

[56] References Cited

U.S. PATENT DOCUMENTS

| | | | |
|---|---|---|---|
| 697,655 | 4/1902 | O'Leary | 220/252 |
| 1,333,051 | 3/1920 | Young | 220/252 |
| 4,375,849 | 3/1983 | Hanifl | |
| 4,534,489 | 8/1985 | Bartlett | |
| 4,657,139 | 4/1987 | Hanifl | |
| 4,702,385 | 10/1987 | Shillington et al. | |
| 4,715,498 | 12/1987 | Hanifl | |
| 4,722,472 | 2/1988 | Bruno | |
| 4,736,860 | 4/1988 | Bemis | |
| 4,779,728 | 10/1988 | Hanifl et al. | |
| 4,828,107 | 5/1989 | Spencer | 220/908 |

*Primary Examiner*—Joseph Man-Fu Moy
*Attorney, Agent, or Firm*—Fishman, Dionne & Cantor

[57] ABSTRACT

A needle and sharps disposal container (10) specifically designed to prevent accidental and intentional contact with biohazardous waste. The disposal container comprising a hollow container body (12) having a barrier means at the top (14) for allowing the deposit of contaminated material while maintaining a constant barrier between the contents of the container and the outside environment. The barrier means includes: a manually rotatable cylinder (22) with a slot (34) rotatable between a downward and an upward position, a slightly larger fixed partial cylinder (24) which surrounds and encases the rotatable cylinder and which provides an elongated convex surface (18) to constrict the rotatable slot (34) through certain degrees of rotation. A torsional spring (46) is provided for biasing the rotatable cylinder toward the downward position to ensure effective disposal of contaminated sharps and needles with each use of the container.

21 Claims, 4 Drawing Sheets

Exploded

NEEDLE DISPOSAL CONTAINER

The present application is a continuation of U.S. application Ser. No. 359,708, filed May 31, 1989, now abandoned.

BACKGROUND—FIELD OF INVENTION

This invention relates to waste containers and specifically to a safer mechanism to dispose of contaminated medical sharps and needles.

BACKGROUND—DESCRIPTION OF PRIOR ART

It is well known that health care workers sustain accidental injury with contaminated intravenous (IV) and syringe needles as well as other sharps. This poses a continually growing threat due to the increasing numbers of HIV or AIDS infected patients. The risk of other infectious diseases such as hepatitis also continues.

Many of the accidental needle sticks occur secondary to unsafe disposal of the contaminated needles. Health care workers are at risk for puncture while reaching into a container, discarding needles into an already full container, and by encountering a needle which has inadvertantly remained at the entry point of the container. Risk is also present to cleaning crews during transportation of full containers in that spilled or dropped containers can be hazardous secondary to removal of the contents of the container. Moreover patients and visitors may be at risk for needle puncture. This is especially true for young children who may unknowingly explore the open containers that contain contaminated needles.

Many if not most health care workers would therefore find it desirable to have the safest possible means for protecting themselves and others from accidental needle or sharp injuries. Heretofore a small number of different disposal containers have been proposed for safer needle and sharp disposal. Cardboard containers with inner plastic bags were proposed but these were unsatisfactory because needles sometimes punctured through the cardboard and because cleaning crews were still at high risk during transportation of the needle-filled plastic bags. U.S. Pat. No. 4,722,472 to Bruno (1988) provided some improvements with a disposable double-walled cardboard container with a hinged top closure. However, the cardboard structure could be weakened with moisture and the hinged door was not designed to prevent someone from reaching into the container.

U.S. Pat. No. 4,736,860 to Bemis (1988) shows a sharps container apparatus with a door manually moveable between an open and closed position with the container being completely closed when the door is in the closed position. This invention provided considerable improvements with the container being made of plastic and with a door that limits access into and out of the container. However there remained three major disadvantages:. when the door is partially open or closed there is access into and out of the container so that contact with contaminated needles could be made, also when the container is overfilled there is the possibility that the door could malfunction in a partially open position, another disadvantage is that an additional step is required to secure the door closed with a manually inserted pin when the container is full.

U.S. Pat. Nos. 4,715,498 and 4,779,728 to Hanifl (1987 and 1988) disclose sharps disposal containers with a recessed top restricted by cowls and a pivotal closure for securing the container when full. However this container permits access to the contents of the container; a child could reach into the container and if the container were to be overturned the contents could be removed. With regard to the latter patent, the container is further limited in that when the apparatus is over filled with waste, needles could overflow at the entry area and thus place users at risk for inadvertant needle sticks during subsequent use of the apparatus.

The sharps disposal containers heretofore known suffer from the following disadvantages: discarded contaminated needles and sharps are not completely isolated from the environment external to the container, before, during and after use of the apparatus, some of the containers require an extra step or procedure to secure the contents of the container prior to disposal, they place the user at risk for needle sticks when they overflow with contaminated sharps, when dropped or overturned the contents of the containers could spill out of the containers, and young children and others could conceivably reach into the containers and sustain inadvertent needle injury from the contents of the container.

Most health care workers, therefore would find it desirable to have a needle disposal mechanism which would allow for safe disposal of contaminated sharps and needles by means of completely isolating the disposed needles from the outside environment before, during and after subsequent use of the apparatus. It would also be desirable to have a container that would not require an extra step to secure the contents after it is full. Similarly it would be advantageous to have a container which would remain secure if overturned and which would not allow a young child or anyone else to reach into the container accidentally or intentionally.

OBJECTS AND ADVANTAGES

Accordingly we claim the following as our objects and advantages of the invention: to provide a disposal container for safe, efficient, and cost-effective disposal of contaminated needles and sharps, to provide a disposal container that will readily dispose of contaminated needles and isolate them permanently within a concealed container so that once they are discarded they are never in contact with the external environment, to provide such a container that requires a minimal amount of time, effort, and skill to use.

In addition we claim the following additional objects and advantages: to provide a needle disposal container which when full will not expose the the user to risk of contact with overflowing contaminated needles, to provide such a container which when full will cease to function while keeping the inner contents of container concealed, to provide a container that requires the user to move only one part of the container one time for the safe deposit of needles into the container, and to provide a container which obviates the need for a procedure to lock the container when it is full.

In addition we claim a needle disposal container with the following additional objects and advantages: to provide a disposal container which when dropped or overturned will keep the already discarded needles and sharps safely secured and confined to the interior of the container, and to provide such a container which will prevent young children and others from tampering with the contents of the container and thus prevent them from making contact with the discarded contaminated needles.

Readers will find further objects and advantages of the invention from a consideration of the ensuing description and the accompanying drawings.

DRAWING FIGURES

FIG. 1 is a front elevational view of the sharps disposal container

FIG. 2 is a top view of the sharps disposal container

FIG. 3 is an enlarged cross-sectional view taken along line 3—3 of FIG. 1

FIGS. 4a-4c are cross-sectional views of the disposal container illustrating the upward, midway, and down positions of the rotatable cylinder FIG. 5 is an exploded view of the stationary and rotatable cylinders FIG. 6 is an isolated front view of the rotatable cylinder in the upward position FIG. 7 is an isolated front view of the rotatable cylinder in the downward position FIG. 8 is an isolated front view of the stationary cylinder

REFERENCE NUMERALS IN DRAWINGS

10—sharps disposal container
12—hollow container body
14—top
18—first elongated convex surface of stationary cylinder
20—second elongated convex surface of stationary cylinder
22—rotatable cylinder
24—stationary cylinder
26—position of rotatable cylinder when it is in the down position
28—level of slot of rotatable cylinder when it is in the upward position
30—external rotating device
32a,b—arms of 30
34—elongated rotatable slot of 22
36—first stationary slot of 24
38—second stationary slot of 24
40—handle of 30
42—horizontal axis of 22
44a,b—axis projections of 22
46—torsional spring
48a,b—rectangular bridging panels of 22
50a,b—circular bridging panels of 22
52a,b—blind bores in 24
54a,b—narrow track slots in 24

BRIEF DESCRIPTION OF THE DRAWING

The invention is described in detail in the following description of a preferred example of the invention.

The sharps disposal container is generally designated 10 in the accompanying figures. The container comprises a rigid, hollow container body 12 and a top 14 permanently attached to the container body 12 as shown in FIG. 3.

Figure 1:
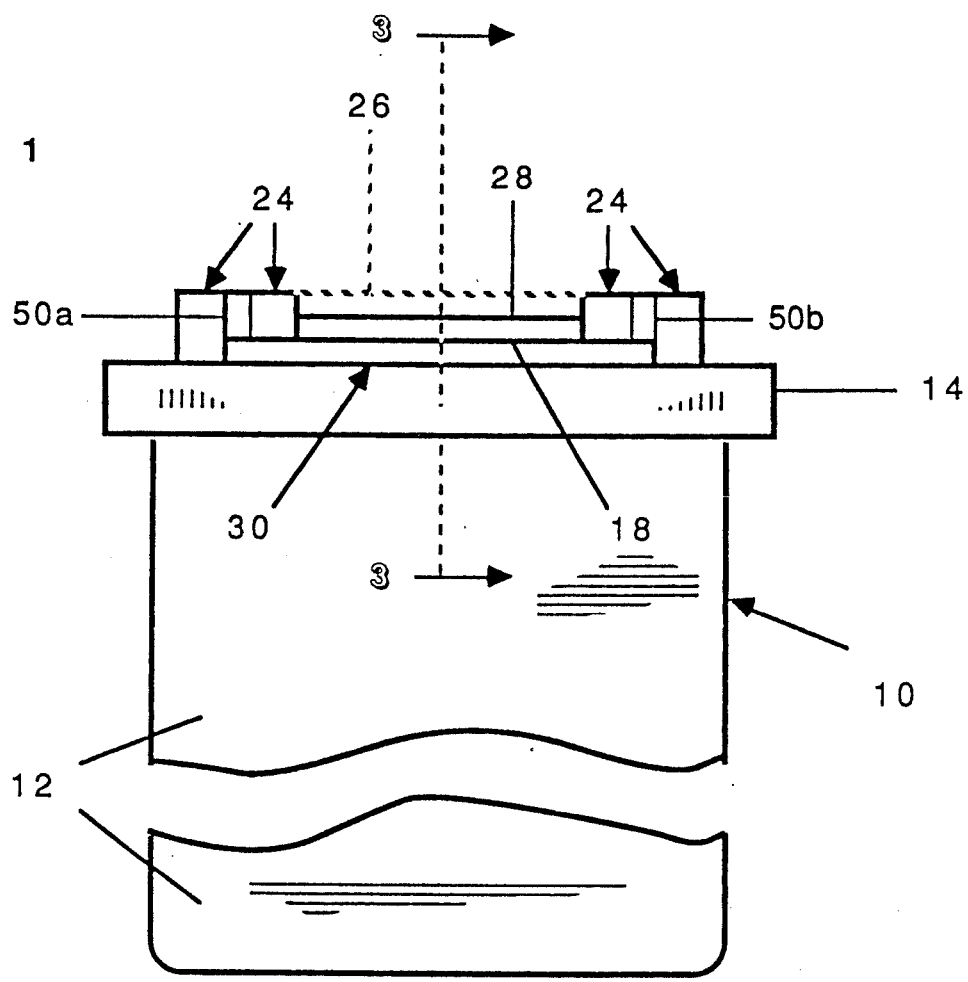
As shown in FIGS. 1, 2, 3, the top 14 is interrupted by a stationary hollow cylinder 24 which is molded to or permanently attached within top 14. The stationary cylinder 24 includes a first stationary elongated slot 36 created by the absence of a rectangular shaped portion removed from its top surface. The stationary cylinder 24 also includes a second stationary elongated slot 38 similarly created by the absence of a rectangular shaped portion removed from the bottom surface of the stationary cylinder 24 (FIGS. 3 and 8). The arc widths of the removed rectangular surfaces creating the first 36 and second 38 stationary slots are each approximately equal to one fourth the circumference of the stationary cylinder 24. The stationary cylinder 24 includes a first elongated convex surface 18 and a second elongated convex surface 20 created by the first 36 and second 38 stationary slots (FIGS. 3 and 8).

The surface arc widths of the first 18 and second 20 elongated convex surfaces are approximately one fourth of the circumference of the stationary cylinder 24. The first elongated convex surface 18 and second elongated convex surface 20 of the stationary cylinder 24 surround and encase the lateral surfaces of the rotatable cylinder 22 as demonstrated in FIG. 3.

A rotatable cylinder 22 is slightly smaller in circumference and length than the stationary cylinder 24 and is located within the boundaries of the first 18 and second 20 elongated convex surfaces of the stationary cylinder 24.

The rotatable cylinder 22 contains a rotatable slot 34 created by the absence of a rectangular shaped portion of its curved surface. The arc width of the absent surface being approximately one fourth the circumference of the rotatable cylinder 22.

The rotatable slot 34 of the rotatable cylinder 22 is approximately equal in width and length to the first stationary slot 36 and to the second stationary slot 38 of the stationary cylinder 24, and approximately equal in width to the width of the first elongated convex surface 18 of the stationary cylinder 24.

Figure 4A:
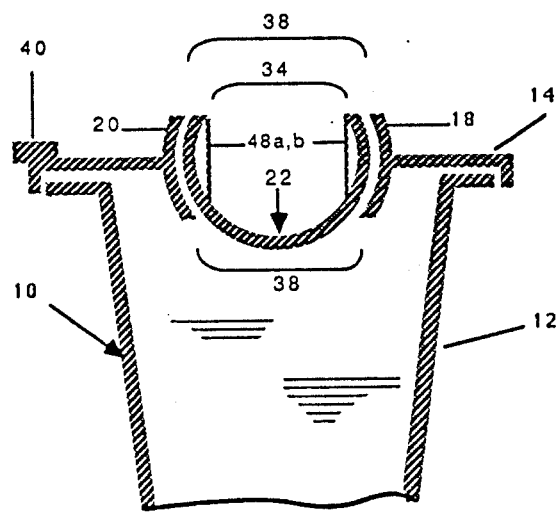
Figure 4B:
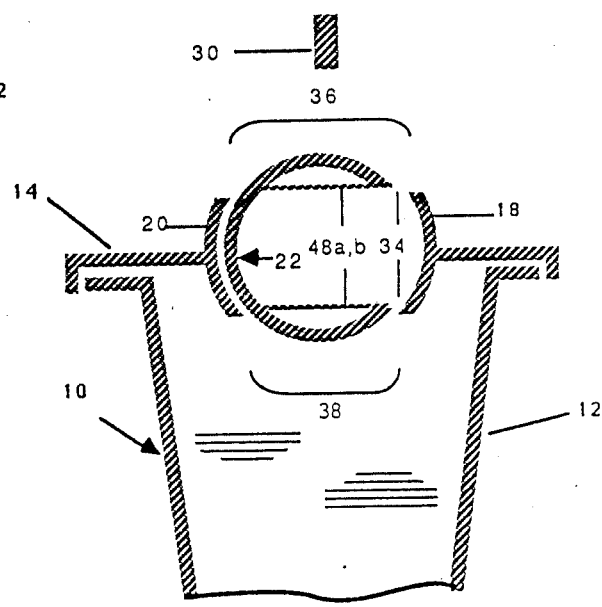

As depicted in FIGS. 4a, b, c the approximate equality in width of all the above mentioned slots 34, 36, 38 and first elongated convex surface 18 allows for (1) alignment of the rotatable slot 34 with the first stationary slot 36 when the rotatable cylinder 22 is in upward position thereby creating an access slot from the outside of the disposal container 10 into the interior of rotatable cylinder 22 (2) alignment of the rotatable slot 34 with the second stationary slot 38 when the rotatable cylinder 22 is in the downward position thus creating an exit slot from interior of the rotatable cylinder 22 to the interior of the container body 12 (3) the first stationary convex surface 18 to cover the rotatable slot 34 when it is in any of the intermediary positions between the full upward position and the full downward position and to completely cover the rotatable slot 34 when it is in the midway position between the upward and downward positions, thus obviating any continuity between the interior of container body 12 and the environment external to the disposal container 10 at any position of the rotatable cylinder.

Figure 7:
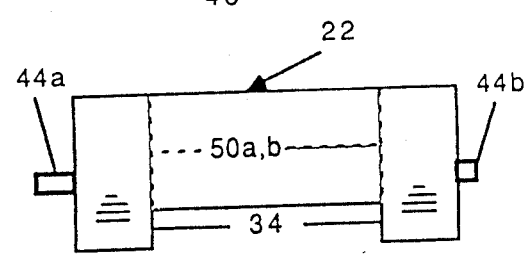

As shown in FIG. 7, the rotatable cylinder 22 is rotatable along a generally horizontal axis 42 within the stationary cylinder 24 by means of two outwardly extending projections 44a, b which are alligned along the horizontal axis 42 on each outside end of the rotatable cylinder 22 and which are receieced by blind complimentary bores 52a, b in the stationary cylinder 24.

Figure 2:
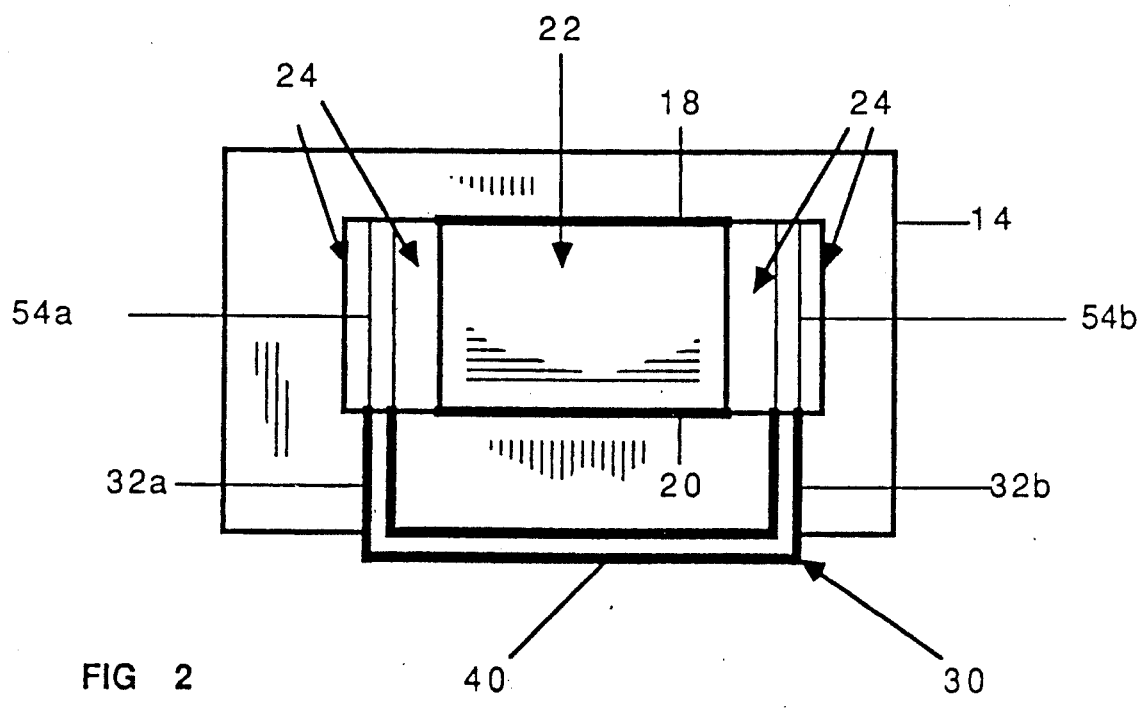

The disposal container 10 includes an external rotating device 30 comprising a crossbar 40 and two arms 32a, b (FIG. 2). The rotating device 30 is attatched to the rotatable cylinder 22 by each of the two arms 32a, b. The arms 32a, b are attached horizontally to the surface of the rotatable cylinder 22 at the level of the horizontal axis 42 when the rotatable cylinder 22 is oriented in the upward or downward position. The crossbar 40 is affixed to the lever arms 32a, b at the opposite ends to the rotatable cylinder 22 such that the crossbar 40 extends slightly over the edge of top 14 when the rotatable cylinder 22 is oriented in the upward or downward position.

Figure 3:
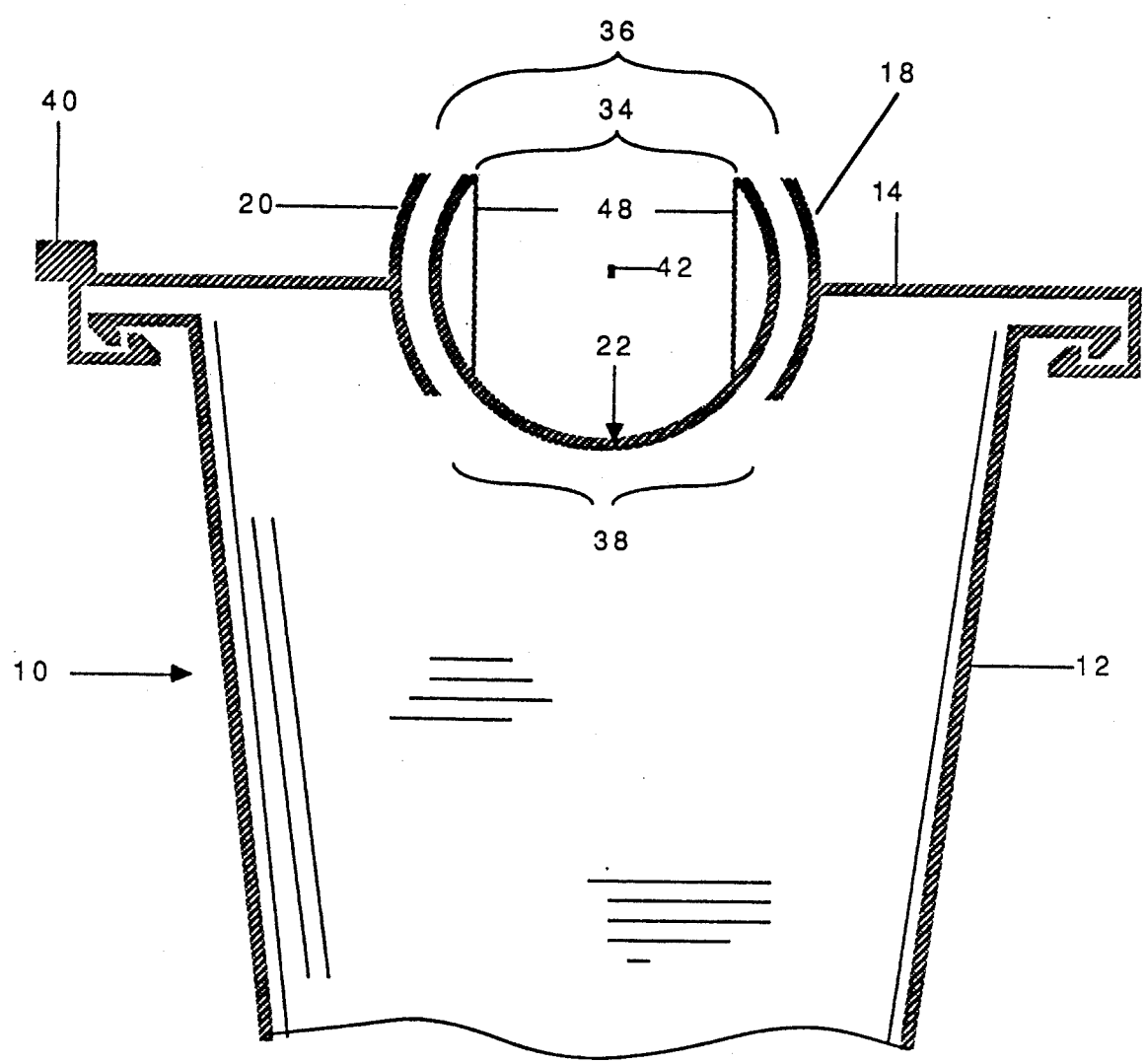

In the upward or downward position, the arms 32a, b and crossbar 40 are oriented in the horizontal position and rest on the top surface of the top 14. In this manner, the top 14 will limit the degree of rotation of the rotatable cylinder 22 by limiting the range of motion of the rotating device 30 by contact at 0 and 180 degrees with respect to the original downward position of the rotatable cylinder 22 as depicted in FIGS. 1, 2, 3.

During repositioning of the rotatable cylinder 22, the arms 32 of rotatng decice 30 pass within the narrow track slots 50a, b of the stationary cylinder 24.

In this manner, the rotating device 30 provides a means for manually positioning the rotatable slot 34 of the rotatable cylinder 22 from the downward position to the upward position for placement of sharps into the interior of the rotatable cylinder 22.

Figure 4C:
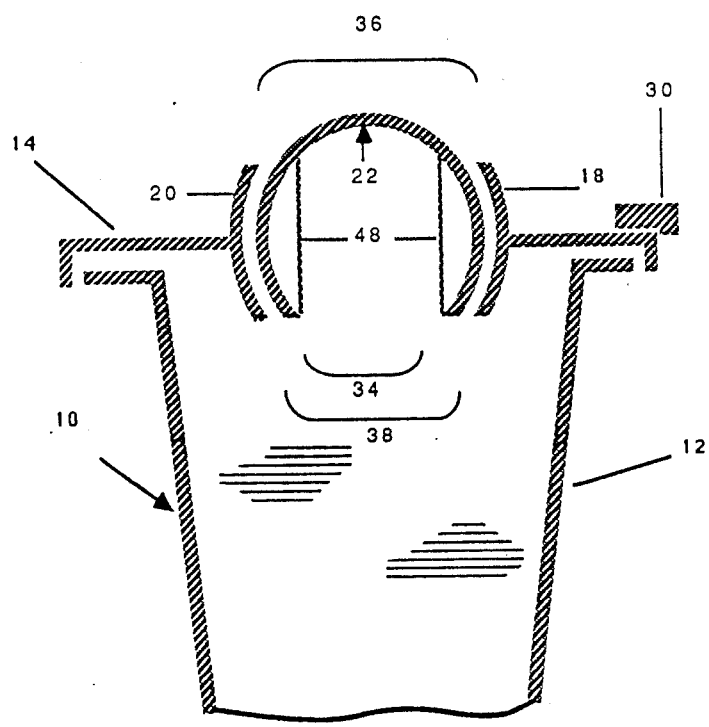
Figure 5:
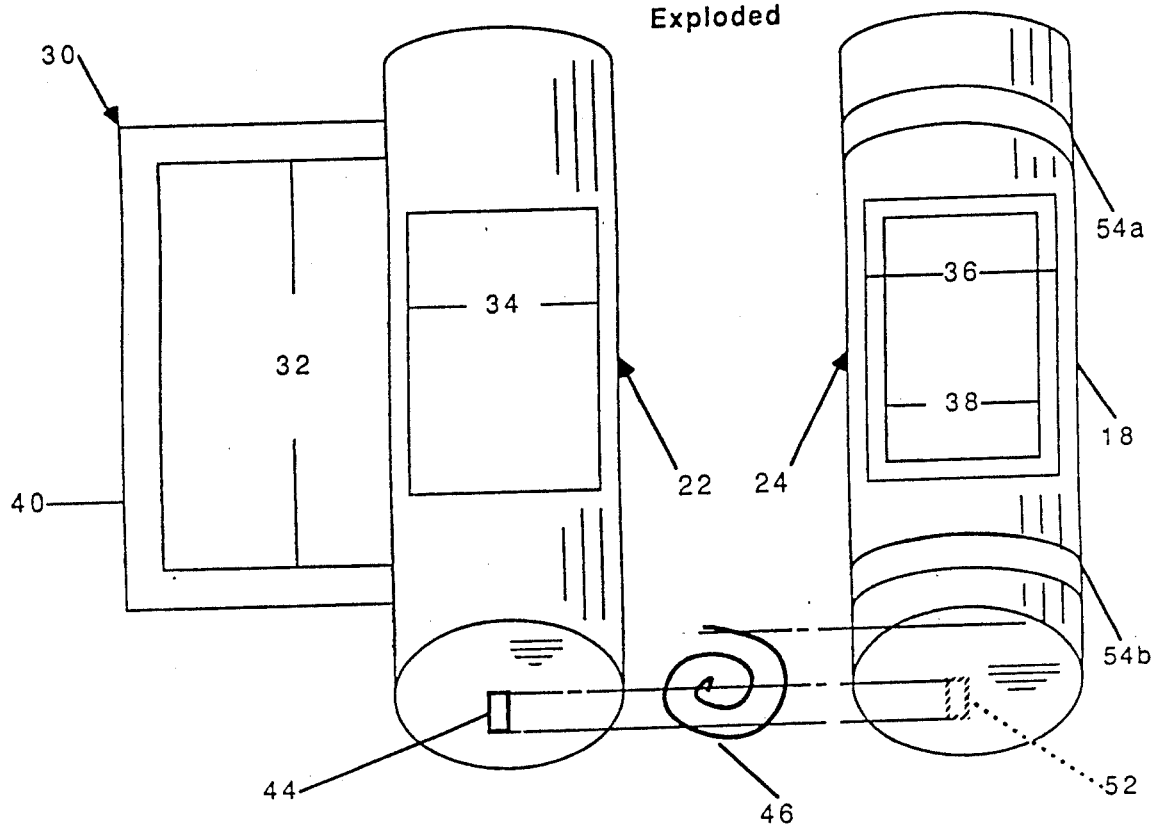
Figure 6:
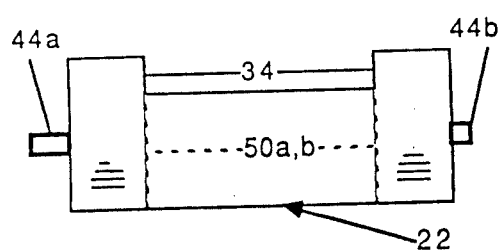

As exemplified in FIG. 5 the sharps disposal container 10 is equipped with a torsional spring 46 positioned between one end surface of the rotatable cylinder 22 and the respective end surface of the stationary cylinder 24. The torsion spring is connected at its center to the outward projection 44a. The other, outer end of torsional spring 46 is connected to the inner surface of the stationary cylinder 24. In this manner the torsional spring 46 exerts force to maintain the rotatable cylinder 22 in the downward position, as in FIG. 4c, when the disposal container 10 is not in use. The torsional spring 46 will also provide recoil force so that when the rotatable container 22 is manually rotated to the upward position (FIG. 4a) the torsional spring 46 is uncoiled thus producing elastic recoil sufficient to return the rotatable cylinder 22 to its original downward position.

Figure 8:
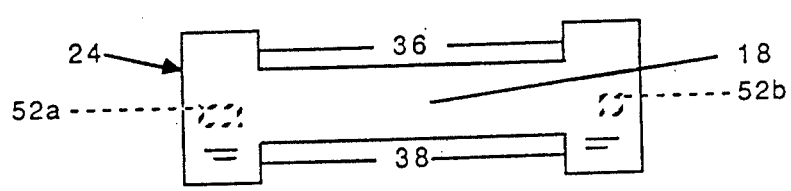

If desired, the rotatable cylinder 22 may be fitted with rectangular internal bridging panels 48a, b (FIGS. 4a, b, c) and circular internal bridging panels 50a, b (FIG. 8) which extend perpendicularly from each of the four surface edges of the elongated slot 34 of rotatable cylinder 22 to the interior surface of the rotatable cylinder 22. In this manner, deposited waste in the rotatable cylinder will be confined to a space with flat boundaries to facilitate exit of the waste from the rotatable cylinder 22 into the interior of the container body 12 when the rotatable cylinder 22 is in the downward position, as seen in FIG. 4c.

It is preferred that the container body 12, top 14, and stationary 24 and rotatable 22 cylinders be molded from an appropriate plastic. If desirable, the stationary 24 and rotatable 22 cylinders can be formed separately from the top 14 and can be permantly or semipermanently snapped into the top 14. If desired, the container body 12 can be made of translucent plastic with a horizontal line drawn across the upper portion of the container body 12 with the word "full" written at that level.

SHARPS DISPOSAL CONTAINER—OPERATION

The sharps disposal container 10 provides a safer means for disposal of sharps and needles and other medical waste. As shown in FIG. 4c the elongated slot 34 of the rotatable cylinder 22 is normally oriented in the downward position while not in use by means of torsional spring 46 (FIG. 5).

The user, wishing to discard sharps, lifts the external rotating device 30 off the surface of top 14 by grasping the crossbar 40 where it extends off the edge of the top 14. The user then pulls the rotating device 30 to the opposite side of the top 14. This movement rotates the rotatable cylinder 22 180 degrees thereby repositioning the rotatable slot 34 to the upward position as shown in FIG. 4a. At this position the rotatable slot 34 is aligned with the first stationary slot 36 of the stationary cylinder 24. The user, while maintaining the rotatable cylinder 22 in this position by holding traction on the rotating device 30 is able drop the sharps through the now aligned first stationary 36 and rotatable 34 elongated slots and thus into the interior of the rotatable cylinder 22.

After the sharps are deposited into the rotatable cylinder 22, the user then releases the rotating device 30 thereby allowing the torsion spring 46 to rotate the rotatable cylinder 22 back to the original downward position, where the second stationary 38 and rotatable 34 elongated slots are aligned (FIG. 4c). In this manner gravity is allowed to force the sharps to exit through the second stationary 38 and rotatable 34 elongated slots, thereby translocating the sharps out of the interior of the rotatable cylinder 22 and into the interior of the sharps disposal container 12. The automatic return of the rotatable cylinder 22 back to its original downward position after use ensures that discarded sharps will be safely and effectively deposited into the interior of the container body 12.

It is preferred that the sharps disposal container 10 be discarded when it becomes full. This time will become evident when the contents reach a height equal to the "full" line on the container body 12 or when the external rotating device 30 is not able to be freely repositioned. At this time, and at any time, the contents of the container body 12 are secured.

The sharps disposal container can be transported by one lifting the external rotating device 30 to the vertical position (90 degree rotation) and then using the crossbar 40 as a carrying handle.

SUMMARY, RAMIFICATIONS, AND SCOPE

Accordingly the reader will see that the sharps disposal container provides for safe and efficient disposal of contaminated needles and sharps; it allows the ongoing disposal of contaminated waste while providing a complete and continuous anterograde and retrograde barrier between the contents of the container and the outside environment. Since the rotatable slot is never open to the interior of the sharps container and to the environment outside of the container simultaneously, the apparatus makes it impossible for anyone, including a small child, to accidentally or intentionally come in contact with needles or sharps inside the disposal container. Similarly, overfilling the container does not place subsequent users at risk for needle injury because the contents of the container remain secure and isolated at all times and because the rotatable cylinder will cease to function when the container is overfilled.

Furthermore the sharps disposal container has the additional advantages in that: it requires the user to move only one part, one time, with one hand for the safe disposal of biohazardous waste, it obviates the need for a procedure to lock the container when it is full because the contents are always secured before, during, and after each use of the container by means the described barrier means, it provides a recoil mechanism to automatically rotate the rotatable cylinder to the downward position after use so that sharps and needles will automatically be deposited into the container with each use.

While the above description contains many specificities, the reader should not construe these as limitations on the scope of the invention, but merely as exemplifications of preferred embodiments thereof. Those skilled in the art will envision many other possible variations within its scope. For example, the dimensions of the container body and the fixed and the rotatable cylinders can be changed; the disposal container can have different shapes such as circular or square instead of rectangular; the rotatable container can be other shapes such as triangular or ovoid in cross section; the rotatable and stationary slots and elongated convexities can be of varying sizes and configurations; the external rotating device can have one arm instead of two, can have circular end pieces on each side of the rotatable container to use as rotating devices, can be attatched to the rotatable cylinder at different places; handles can be made in the top or the container body for transportation; the sharps disposal container can include a wall bracket which can secure the entire sharps container; a torsion spring can be placed on each side of the rotatable cylinder; the torsion spring can be replaced by an elastic band or other spring mehanism to produce the same effect; the rotatable cylinder could surround and encase the fixed cylinder; the elongated convexity could function alone or as a component of an object other than the stationary cylinder; the rotatable and fixed cylinders can be positioned at higher or lower levels within the top. In addition, the bridging panels can be made to form open spaces other than the rectangular space described, i.e., triangular.

Another variation is to have the top and/or the rotatable and stationary cylinders be reusable from continer to container; the user would dispose of the full container body with a different secured top.

Accordingly the reader is requested to determine the scope of the invention by the appended claims and their legal equivalents, and not by the examples which have been given.

What is claimed is:

1. A disposal container comprising:
   a. a hollow container body;
   b. a top;
   c. a complete barrier means positioned within said top allowing the deposit of waste material into the interior of said container body while also maintaining a constant and complete barrier between the interior of the container body and the environment outside of the disposal container at all times, said barrier means comprising:
      i. a rotatable cylinder rotatably secured to said top, said rotatable cylinder being rotatable around a horizontal axis, at least a portion of the rotatable cylinder comprising a rotatable slot; said rotatable slot being of dimensions not larger than the dimensions of said curved surface such that the rotatable slot is never open to the inside of the container body and to the environment outside said disposal container simultaneously during any degree of rotation of said rotatable cylinder, and said stationary curved surface completely covering said rotatable slot at some degree of rotation of said rotatable cylinder,
      ii. a stationary elongated curved surface affixed to said top, said curved surface being of dimension equal to or greater than said rotatable slot, said curved surface preventing direct communication between environment outside of the container and the inside of the container at all degrees of rotation of the cylinder; and
   d) an external rotating device affixed to said rotatable cylinder whereby said rotatable cylinder can be rotated around said horizontal axis.

2. A disposal container according to claim 1 wherein said external rotating device includes a handle attached to said rotatable cylinder.

3. A disposal container set forth in claim 1 wherein said rotatable cylinder is positioned horizontally within said top and rotatable back and forth between a downward position and an upward position with respect to said rotatable slot being oriented in a downward position and an upward position.

4. A disposal container according to claim 3 wherein said stationary curved surface conforms to the longitudinal surface of said rotatable cylinder and restricts access through said rotatable slot when said rotatable cylinder is in intermediary positions between said upward and said downward positions.

5. A sharps disposal container set forth in claim 3 wherein said rotatable cylinder includes a means for biasing said rotatable cylinder toward said downward position.

6. A sharps disposal container as set forth in claim 5 wherein the biasing means includes a torsional spring.

7. A sharps disposal container set forth in claim 3 wherein said rotatable cylinder further comprising planar boundaries, each boundary extending from each side of the surface perimeter of said rotatable slot to the interior surface of the rotatable container, the planar boundaries thereby defining an open compartment with flat boundaries within said rotatable cylinder so as to ensure effective exit of the contents of said rotatable cylinder when said rotatable cylinder is oriented in said downward position.

8. A disposal container according to claim 3 wherein said rotatable slot being created by the absence of an elongated portion of curved surface from said rotatable cylinder, the arc width of said rotatabe slot being approximately equal to the arc width of said stationary curved surface.

9. A sharps disposal container set forth in claim 8 wherein said stationary curved surface further surrounding and encasing a portion of the surface of said rotatable cylinder, said elongated curved surface completely covering said rotatable slot when the rotatable slot is oriented in a midway position between the downward position and the upward position.

10. A disposal container according to claim 9 wherein said stationary curved surface comprises a portion of a stationary cylinder, said stationary cylinder including a first stationary slot in the top of said stationary cylinder and a second stationary slot in the bottom of said stationary cylinder, the first slot and the second slot defining therebetween the stationary curved surface on one side of said stationary cylinder.

11. A disposal container according to claim 10 wherein the arc widths of said first stationary slot and said second stationary slot and said stationary curved surface all being approximately equal to one fourth the circumference of said stationary cylinder and the arc width of said rotatable slot being approximately equal to one fourth the circumference of said rotatable cylinder.

12. A disposal container according to claim 10 wherein said stationary cylinder also provides a second stationary elongated curved surface complimentary to said elongated curved surface and positioned adjacent to said rotatable cylinder on the side of said rotatable cylider opposite to said stationary curved surface.

13. A disposal container comprising:
a) a hollow container body;
b) a top;
c) a complete barrier means, positioned within said top, for isolating needles deposited into said hollow container body so that said needles are completely isolated and secure from the environment outside said disposal container, at least a portion of said barrier means comprising;
  i. a rotatable cylinder positioned within said top, at least a portion of said rotatable cylinder comprising a rotatable slot in the surface of said rotatable cylinder, said rotatable cylinder being rotatable around an horizontal axis between an upward and downward position with respect to said rotatable slot being oriented in an upward and a downward position, said rotatable slot permitting access from the environment outside said disposal container to the interior of said rotatable cylinder when said rotatable cylinder is in the upward position, said rotatable slot also permitting access from the interior of said rotatable cylinder to the interior of said hollow container body when said rotatable cylinder is positioned in the downward position;
  ii. a stationary curved surface affixed to the top and adjacent to a portion of the rotatable cylinder to prevent communication between the environment outside said container and the interior of said hollow container body through said rotatable slot when said rotatable cylinder is in intermediary positions between the downward position and the upward position, said curved surface not smaller in dimension than said rotatable slot so that said rotatable slot is never open to the environment outside of said disposal container and to the interior of said container body simultaneously; and
d) an external rotating device whereby said rotatable cylinder can be rotated around said horizontal axis.

14. A sharps disposal container according to claim 13 wherein said stationary curved surface is affixed horizontally to said top, said elongated curved surface being positioned alongside the rotatable cylinder so as to prevent said rotatable slot from being open to the environment outside of said disposal container and open to the interior of said container body, simultaneously.

15. A sharps disposal container according to claim 14 wherein said stationary curved surface comprises a lateral curved surface of a stationary cylinder, the stationary curved surface being created by a first stationary slot in the top of said stationary cylinder and a second stationary slot in the bottom of said stationary cylinder, the first and second stationary slots defining the stationary curved surface therebetween on one side of the stationary cylinder, the width of said stationary curved surface being approximately equal to the width of said rotatable slot.

16. A sharps disposal container according to claim 15 wherein said rotatable cylinder is slightly smaller than and positioned within said stationary cylinder.

17. A sharps disposal container according to claim 13 wherein said rotatable slot and said elongated curved surace are rectangular in outline and are approximately equal in width and length, the arc width of said rotatable slot being approximately equal to one fourth the circumference of said rotatable cylinder.

18. A Sharps disposal container comprising:
a) a hollow container body;
b) a top;
c) a complete barrier means, positioned within said top, for allowing the deposit of needles into the interior of said container body while also maintaining a complete physical barrier between the inside of said container body and the outside of said sharps disposal container at all times, at least a portion of said barrier means comprising;
  i. a rotatable cylinder positioned within said top and including a rotatable slot in the surface of said rotatable cylinder, said rotatable slot providing access into and out of said rotatable cylinder, said rotatable cylinder being rotatable around horizontal axis between a downward position and an upward position with respect to the orientation of said rotatable slot in an upward position and a downward position, said container body being completely closed to the enviroment outside of said sharps container when said rotatable cylinder is in the upward position, in the downward position and in any position in between the upward and the downward positions;
  ii. an elongated curved surface affixed to said top and disposed adjacent to and conformorming to the longitudinal surface of said rotatable cylinder so as to prevent direct communication between the outside of the container and the inside of the container through the rotatable slot when the rotatable cylinder is in intermediary positions between the upward position and the downward position, said elongated curved surface completely covering said rotatable slot when said rotatable cylinder is rotated approximately 90 degrees from the upward position toward the downward position and when said rotatable cylinder is rotated approximately 90 degrees from the downward position toward the upward position, said elongated curved surface is of large enough dimension to prevent the rotatable slot from being open to the environment outside of said sharps disposal container and open to the interior of said container body simultaneously; and
d) an external rotating device whereby said rotatable cylinder can be rotated around the horizontal axis.

19. A sharps disposal container according to claim 18 wherein said elongated curved surface is affixed horizontally to said top, said elongated curved surface being of an arc width approximately equal to one fourth the circumference of said rotatable cylinder and approximately equal to the arc width of said rotatable slot.

20. A sharps disposal container according to claim 18 wherein said barrier means includes a second stationary elongated curved surface attached to said top adjacent to said rotatable cylinder on the opposite side than said elongated curved surface.

21. A disposal container for medical sharps, comprising:
- barrier means for partitioning an inner chamber from an external environment, said barrier means comprising:
  - a receptacle member having a continuous sidewall extending from a closed end to an open end;
  - a cover member for covering said open end, said cover portion being removably secured to said receptacle member and defining an opening therethrough;
- transfer means for transferring the sharps from the external environment into the inner chamber, said transfer means comprising:
  - a longitudinally extending cylindrical member rotatably mounted on said cover member to cover said opening, said cylindrical member defining a transfer chamber therein and defining a transfer opening communicating with the transfer chamber, wherein said cylindrical chamber is rotatable so that the transfer opening sweeps out a first arc wherein the transfer opening communicates between the external environment and the transfer chamber and sweeps out a second arc wherein the transfer opening communicates between the inner chamber and the transfer chamber; and
- isolation means for preventing direct communication between the inner chamber and the external environment during transfer of the sharps from the external environment into the inner chamber; said isolation means comprising:
- wall members, secured along said opening in said top portion, for covering said transfer opening to prevent said transfer opening from simultaneously communicating with said external environment and with said inner chamber.

* * * * *